United States Patent
Kumazaki et al.

(10) Patent No.: US 8,324,596 B2
(45) Date of Patent: Dec. 4, 2012

(54) TOTAL INTERNAL REFLECTION FLUORESCENCE (TIRF) OBSERVATION DEVICE

(75) Inventors: Nobutaka Kumazaki, Hitachinaka (JP); Satoshi Takahashi, Hitachinaka (JP); Hirokazu Kato, Mito (JP); Takanobu Haga, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 8 days.

(21) Appl. No.: 13/055,854

(22) PCT Filed: May 20, 2009

(86) PCT No.: PCT/JP2009/059635
§ 371 (c)(1),
(2), (4) Date: Jan. 25, 2011

(87) PCT Pub. No.: WO2010/010751
PCT Pub. Date: Jan. 28, 2010

(65) Prior Publication Data
US 2011/0121204 A1    May 26, 2011

(30) Foreign Application Priority Data
Jul. 25, 2008    (JP) ................. 2008-191581

(51) Int. Cl.
*G01N 21/64* (2006.01)
(52) U.S. Cl. .................. 250/459.1
(58) Field of Classification Search ........ 250/459.1
See application file for complete search history.

(56) References Cited

U.S. PATENT DOCUMENTS

| 6,255,642 B1 * | 7/2001 | Cragg et al. .......... 250/216 |
| 2005/0179903 A1 | 8/2005 | Tsuruta et al. |
| 2006/0157637 A1 | 7/2006 | Karasawa et al. |
| 2008/0179491 A1 | 7/2008 | Karasawa et al. |

FOREIGN PATENT DOCUMENTS

JP    03-246452    11/1991
(Continued)

OTHER PUBLICATIONS

Funatsu, T., et al., "Imaging of single fluorescent molecules and individual ATP turnovers by single myosin molecules in aqueous solution", Letters Nature, Apr. 6, 1995, pp. 555-559, vol. 374.
Braslavsky, I., et al., "Sequence information can be obtained from single DNA molecules", PNAS, Apr. 1, 2003, pp. 3960-3964, vol. 100 No. 7.

(Continued)

*Primary Examiner* — Kiho Kim
(74) *Attorney, Agent, or Firm* — McDermott Will & Emery LLP

(57) ABSTRACT

A device and method for fluorescence observation have good operability, high sensitivity, and high acid reliability. The device is used for fluorescence observation using evanescent light. The angle of incidence of the excitation light is adjusted so that the excitation light is totally reflected from the surface of a substrate irrespective of the angle of the substrate surface. The method includes a step of shining the excitation light on the observation substrate while continuously varying the angle of the excitation light with respect to the observation substrate. In addition, the method includes a step of sensing the shone excitation light via optical sensors, and a step of setting the angle of total reflection according to the result of the sensing by the optical sensors. In the present device and method, the direction in which the shone excitation light travels varies with the angle of incidence.

12 Claims, 6 Drawing Sheets

FOREIGN PATENT DOCUMENTS

| | | | |
|---|---|---|---|
| JP | 3-246452 A | | 11/1991 |
| JP | 2006080446 | * | 3/2006 |
| JP | 2006-189741 | | 7/2006 |
| JP | 2006-189741 A | | 7/2006 |
| JP | 2006-201465 | | 8/2006 |
| JP | 2006-201465 A | | 8/2006 |

OTHER PUBLICATIONS

Japanese Office Action with English Translation issued in Japanese Application No. 2010-521633 issued on Jun. 12, 2012.

* cited by examiner

TOTAL INTERNAL REFLECTION FLUORESCENCE (TIRF) OBSERVATION DEVICE

RELATED APPLICATIONS

This application is the U.S. National Phase under 35 U.S.C. §371 of International Application No. PCT/JP2009/059635, filed on May 20, 2009, which in turn claims the benefit of Japanese Application No. 2008-191581 filed on Jul. 25, 2008, the disclosures of which Applications are incorporated by reference herein.

TECHNICAL FIELD

The present invention relates to a device that performs fluorescence observation using total reflection illumination.

BACKGROUND ART

When a living organism substance such as DNA or protein is observed, it is a general practice to use a method of performing marking with a fluorescent dye, irradiating excitation light such as a laser, and observing generated fluorescent light. In recent years, as a technique that can measure fluorescent light at a molecular level, there is an observation method employing evanescent light (Non Patent Literature 1). When light having an angle equal to or larger than a fixed angle is made incident from a medium having a high refractive index to a medium having a low refractive index, the incident light does not diffuse to the medium having the low refractive index and total reflection occurs. At this point, a phenomenon in which the light slightly oozes out occurs on a surface on the low-refractive index medium side of a boundary surface. The oozing-out light is called evanescent light. The intensity of the evanescent light is attenuated exponentially further away from a refractive index boundary plane. Excitation light intensity is 1/e at a distance of about 150 nm from the refractive index boundary plane. Therefore, by fixing an observation sample to the boundary surface, it is possible to irradiate the excitation light only on the sample near the boundary surface. Background light deriving from a free phosphor, Raman scattering of water, or the like is suppressed and a high-contrast image is obtained.

Further, there is proposed DNA sequencing employing the technique of one-molecular fluorescence detection explained above (Non Patent Literature 2). Sample DNA fragments that should be analyzed are captured at random by one molecule at a time on a substrate surface and expanded by substantially one base at a time. This is measured by the fluorescence detection employing the evanescent light to determine a base sequence. Specifically, a single target molecule is fixed on a solution layer side on the refractive index boundary plane by using protein binding of biotin and avidin. The target DNA molecule is captured into mold DNA as a matrix of DNA polymerase. A DNA chain extension reaction can be stopped by the presence of a protecting group. A step of performing a DNA polymerase reaction using four kinds of dNTP derivatives (MdNTP) having marks that could be detected, a step of sensing the captured MdNTP with fluorescent light or the like, and a step of returning the MdNTP to an extendable state are set as one cycle. A base sequence of sample DNA is determined by repeating the cycle.

The evanescent light irradiation has an advantage that it is possible to observe a low-background and faint signal but, on the other hand, has a disadvantage that complicated and accurate optical adjustment (for strictly controlling an angle of incidence (AOI)) is necessary and indispensable. As means for solving the problem, the total internal reflection fluorescence (TIRF) microscope described in Patent Literature 1 includes the mechanism for keeping oozing depth of the evanescent light constant. Specifically, an angle of incidence of excitation light is automatically controlled on the basis of relation information between an angle of incidence of the excitation light and oozing depth of the evanescent light recorded in advance so that oozing depth designated by a user is obtained.

The total internal reflection fluorescence (TIRF) X-ray analysis device described in Patent Literature 2 includes the means for properly setting an angle of incidence of excitation light. Specifically, excitation X-ray is shone on a sample on a substrate, the intensity of a reflected X-ray reflected on the surface of the substrate is measured by a sensor, and an angle of incidence of the excitation X-ray is controlled on the basis of the intensity.

CITATION LIST
PATENT LITERATURE
PATENT LITERATURE 1: JP-A-2006-189741
PATENT LITERATURE 2: JP-A-03-246452
NON PATENT LITERATURE
NON PATENT LITERATURE 1: Nature 1995, Vol. 374, pp. 555-559.
NON PATENT LITERATURE 2: PNAS 2003, Vol. 100, pp. 3960-3964.

SUMMARY OF INVENTION

Technical Problem

However, although the angle adjusting function described in Patent Literature 1 is effective for a completely flat substrate, waviness and roughness are locally present on an actual substrate surface and local unevenness is also present. Therefore, an angle of incidence varies in each shining area. As a result, excitation light intensity is not fixed and fluctuation occurs in observation results. This function can keep a total reflection angle constant. However, if an angle of incidence of excitation light is larger than a critical angle even if the excitation light is totally reflected, the depth of the oozing of the evanescent light is small. Even if the substrate is completely flat and the angle of incidence can be kept constant, if a difference between the angle of incidence and the critical angle is large, the depth of the oozing of the evanescent light is small because of the large difference. Therefore, sufficient excitation light intensity is not obtained. As a result, fluorescent intensity of a measurement object falls.

Further, in the total internal reflection fluorescence (TIRF) observation device described in Patent Literature 2, when a difference between a refractive index of a substrate and a refractive index of a medium is larger or depending on a surface state of the substrate, for example, even in a transmission state, reflection partially occurs on the substrate surface. In other words, since reflected light is present even if the surface state is a total reflection state, in some case, it is difficult to distinguish partially reflected light and totally reflected light simply by detecting the reflected light.

It is an object of the present invention to provide a fluorescence observation method and a fluorescence observation device that have high operability, high sensitivity, and high reliability.

Means for Solving Problem

In the present invention, concerning a device that performs fluorescence observation using evanescent light, an angle of incidence of excitation light is adjusted so that the excitation light is always totally reflected on a substrate surface irrespective of an angle of the substrate surface. This method includes a step of making excitation light incident on an observation surface while continuously varying an angle of the excitation light, a step of sensing the excitation light after the incidence with an optical sensor, and a step of setting a total reelection angle from a sensing result of the optical sensor.

In the present invention, concerning a device that performs fluorescence observation using evanescent light, an angle of incidence of excitation light is adjusted so that the excitation light is always totally reflected on a substrate surface irrespective of local irregularities of a substrate surface. This method includes a step of irradiating the excitation light on an observation substrate at an arbitrary angle of incidence, a step of sensing the excitation light after the incidence with an optical sensor, a step of determining a present state of an angle of incidence on the basis of a sensing result of the optical sensor, and a step of adjusting an angle of incidence of the excitation light on the basis of a result of the determination so that the excitation light is totally reflected on a substrate surface.

A traveling direction of excitation light shone on a substrate changes according to an angle of incidence of the excitation light. In other words, the excitation light changes to transmitted light, reflected light, and surface diffusing light. These lights are sensed by optical sensors respectively corresponding thereto, whereby it is determined in what kind of state the angle of incidence of the excitation light is with respect to a critical angle, the angle of incidence of the excitation light is varied on the basis of a result of the determination, and an optimum total reflection angle is realized.

In one embodiment, excitation light after being shone on a substrate is sensed by three optical sensors, whereby an angle of total reflection is automatically set. This method includes a step of irradiating the excitation light on a measurement target area, a step of continuously varying an angle of incidence, a step of sensing three states (transmission, reflection, and surface diffusion) of the excitation light after incidence with optical sensors respectively corresponding to the states, and a step of appropriately setting an angle of incidence of the excitation light on the basis of a sensing result so that the excitation light is totally reflected on a substrate surface.

In another embodiment, excitation light after being shone on a substrate is sensed by three optical sensors, whereby an angle of incidence of the excitation light for realizing total reflection illumination is automatically set. This method includes a step of irradiating the excitation light on a measurement target area, a step of sensing transmitted light, reflected light, or surface diffusing light generated as a result of the irradiation with optical sensors respectively corresponding to the lights, a step of determining a present state of incident light on the basis of a sensing result, a step of varying an angle of incidence of the excitation light on the basis of a determination result, and a step of continuously performing the steps until the excitation light is totally reflected on a substrate surface.

In still another embodiment, an angle of total reflection is automatically set by detecting excitation light after being shone on a substrate with one optical sensor. This method includes a step of leading transmitted light, reflected light, and surface diffusing light to the one optical sensor, a step of sensing presence or absence of signals of the lights in areas sectioned in the one sensor, and a step of appropriately setting an angle of incidence of the excitation light on the basis of a sensing result so that the excitation light is totally reflected on a substrate surface.

In still another embodiment, an angle of incidence of excitation light for realizing total reflection illumination is automatically set by detecting the excitation light after being shone on a substrate with one optical sensor. This method includes a step of irradiating the excitation light on a measurement target area, a step of leading transmitted light, reflected light, or surface diffusing light generated as a result of the irradiation to the one optical sensor, a step of sensing presence or absence of the lights in areas sectioned in the one sensor, a step of determining a present state of an angle of incidence on the basis of a sensing result, a step of varying an angle of incidence of the excitation light on the basis of a determination result, and a step of continuously performing the steps until the excitation light is totally reflected on a substrate surface.

In still another embodiment, an angle of total reflection is automatically set by detecting excitation light after being shone on a substrate with two optical sensors. This method includes a step of sensing, among transmitted light, reflected light, and surface diffusing light, two kinds including the surface diffusing light with optical sensors corresponding to the two kinds, and a step of appropriately setting an angle of incidence of the excitation light on the basis of a sensing result so that the excitation light is totally reflected on a substrate surface.

In still another embodiment, an angle of incidence of excitation light for realizing total reflection illumination is automatically set by detecting the excitation light after being shone on a substrate with two optical sensors. This method includes a step of irradiating the excitation light on a measurement target area, a step of sensing, among transmitted light, reflected light, and surface diffusing light generated as a result of the irradiation, two kinds of light including the surface diffusing light with optical sensors respectively corresponding to the two kinds of light, a step of determining a present state of an angle of incidence on the basis of a sensing result, a step of varying an angle of incidence of the excitation light on the basis of a determination result, and a step of continuously performing the steps until the excitation light is totally reflected on a substrate surface.

In still another embodiment, an angle of total reflection is automatically set by detecting excitation light after being shone on a substrate with one optical sensor. This method includes a step of leading, among transmitted light, reflected light, and surface diffusing light, two kinds including the surface diffusing light to the one optical sensor, a step of sensing presence or absence of signals of the respective lights in areas sectioned in the one sensor, and a step of appropriately setting an angle of incidence of the excitation light on the basis of a sensing result so that the excitation light is totally reflected on a substrate surface.

In still another embodiment, an angle of incidence of excitation light for realizing total reflection illumination is automatically set by detecting the excitation light after being shone on a substrate with one optical sensor. This method includes a step of irradiating the excitation light on a measurement target area, a step of leading, among transmitted light, reflected light, and surface diffusing light generated as a result of the irradiation, two kinds of light including the surface diffusing light to the one optical sensor, a step of sensing presence or absence of the lights in areas sectioned in the one sensor, a step of determining a present state of an angle of incidence on the basis of a sensing result, a step of varying an angle of incidence of the excitation light on the basis of a determination result, and a step of continuously performing the steps until the excitation light is totally reflected on a substrate surface.

In still another embodiment, an angle of total reflection is automatically set by detecting excitation light after being shone on a substrate with one optical sensor. This method includes a step of sensing surface diffusing light with the optical sensor and a step of appropriately setting an incident light of the excitation light on the basis of a sensing result so that the excitation light is totally reflected on a substrate surface.

In still another embodiment, an angle of incidence of excitation light for realizing total reflection illumination is automatically set by detecting excitation light after being shone on a substrate with one optical sensor. This method includes a step of irradiating the excitation light on a measurement target area, a step of sensing surface diffusing light generated as a result of the irradiation with the optical sensor, a step of determining a present state of an angle of incidence on the basis of a sensing result, a step of varying an angle of incidence of the excitation light on the basis of a determination result, and a step of continuously performing the steps until the excitation light is totally reflected on a substrate surface.

Advantageous Effects of Invention

According to the present invention, since it is possible to automatically set an angle of incidence so that excitation light is totally reflected, operability is improved. Since an optimum angle of incidence can be always controlled without depending on a surface state of an observation area, reliability is improved compared with the conventional method. Further, since the angle of incidence is not set smaller than necessary, it is possible to keep evanescent light intensity high. As a result, it is possible to obtain high signal intensity compared with the conventional method.

DESCRIPTION OF EMBODIMENTS

Figure 1:
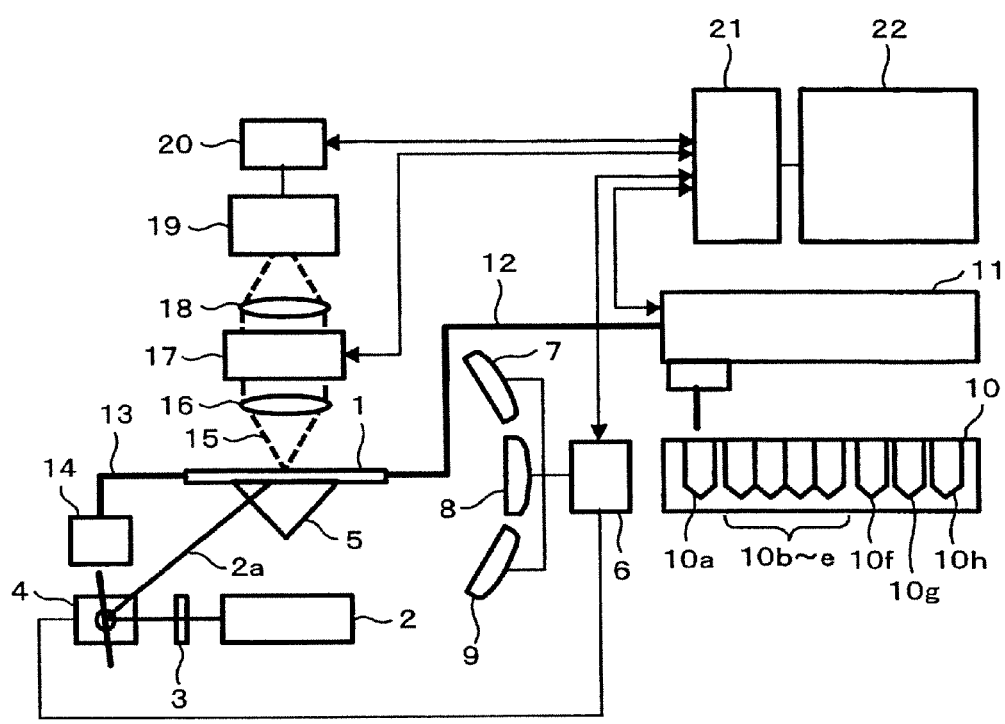
FIG. 1 is an explanatory diagram of a device in a first embodiment.

The new characteristics explained above and other new characteristics of the present invention are specifically explained below with reference to embodiments. However, the present invention is not limited to these embodiments and various changes, improvements, and combinations of the embodiments are possible.

The embodiments disclose a total internal reflection fluorescence (TIRF) observation device including a substrate, on the surface of which a measurement sample is arranged, a light source that irradiates excitation light on the substrate, a detector that measures emitted light generated from the substrate, an optical sensor that senses the excitation light after being shone on the substrate, and an adjusting device that adjusts an angle of incidence (AOI) of the excitation light on the basis of a sensing result of the optical sensor.

The embodiments disclose a method of automatically adjusting an angle of incidence of excitation light in a device that performs fluorescence observation using total reflection illumination, the method including: continuously varying the angle of incidence of the excitation light with respect to a substrate, on the surface of which a measurement sample is arranged; sensing, with an optical sensor, at least one of transmitted light, surface diffusing light, and reflected light generated by incidence of the excitation light on the substrate; and an angle of incidence control mechanism adjusting the angle of incidence of the excitation light on the basis of a sensing pattern of the optical sensor so that the angle of incidence is a total reflection angle.

The embodiments disclose a method of automatically adjusting an angle of incidence of excitation light in a device that performs fluorescence observation using total reflection illumination, the method including: continuously varying the angle of incidence of the excitation light with respect to a substrate, on the surface of which a measurement sample is arranged; sensing, with an optical sensor, at least one of transmitted light and surface diffusing light generated by incidence of the excitation light on the substrate; and an angle of incidence control mechanism adjusting the angle of incidence of the excitation light on the basis of a sensing pattern of the optical sensor so that the angle of incidence is a total reflection angle.

The embodiments disclose a method of automatically adjusting an angle of incidence of excitation light in a device that performs fluorescence observation using total reflection illumination, the method including: continuously varying the angle of incidence of the excitation light with respect to a substrate, on the surface of which a measurement sample is arranged; sensing, with an optical sensor, at least one of surface diffusing light and reflected light generated by incidence of the excitation light on the substrate; and an angle of incidence control mechanism adjusting the angle of incidence of the excitation light on the basis of a sensing pattern of the optical sensor so that the angle of incidence is a total reflection angle.

The embodiments disclose a method of automatically setting an angle of incidence of excitation light in a device that performs fluorescence observation using total reflection illumination, the method including: continuously varying the angle of incidence of the excitation light with respect to a substrate, on the surface of which a measurement sample is arranged; sensing, with an optical sensor, surface diffusing light generated by incidence of the excitation light on the substrate; and an angle of incidence control mechanism adjusting the angle of incidence of the excitation light on the basis of a sensing pattern of the optical sensor so that the angle of incidence is a total reflection angle.

The embodiments disclose that the substrate is formed of a member that transmits light.

The embodiments disclose that the excitation light after being shone on the substrate includes transmitted light, surface diffusing light, and reflected light.

The embodiments disclose that the optical sensor senses any one of transmitted light, surface diffusing light, and reflected light or a combination of the lights.

The embodiments disclose that the control mechanism determines a present state of an angle of incidence from a combination of sensing results of transmitted light, surface diffusing light, and reflected light.

The embodiments disclose that the control mechanism includes an algorithm for instructing, on the basis of the present state of the angle of incidence, a driving mechanism to perform next operation.

[First Embodiment]

FIG. 1 is a diagram of a DNA base sequence analysis device having an angle adjusting function in this embodiment. The device has a configuration like an erecting microscope. The device measures, in fluorescence detection, fluorescent molecules captured on a substrate 1. It is also possible to configure the device as an inverted microscope. When this operation is based on a unimolecular fluorescence detecting method, measurement is performed in an environment like a clean room via an HEPA filter.

A series of reaction is performed on reaction substrate 1. The substrate 1 is made of a transparent material. As the material, for example, synthetic quartz can be used. Plural primers are fixed to the substrate. For example, a 5' terminal end of the primers is biotinylated and a substrate surface is avidinated. The primers are fixed to the surface of the substrate 1 using biotin-avidin binding. The primers may be arranged on the substrate at random. However, it is desirable to regularly arrange the primers taking into account efficiency during observation.

A laser beam 2a from a laser device 2 for fluorescence excitation (YAG laser, 532 nm) passes through a quarter-wave plate 3 to change to circularly polarized light and is made incident on a prism 5 made of quartz for total reflection illumination via a mirror unit 4 and shone from the rear side of the substrate 1. The prism 5 made of quartz and the substrate 1 are set in contact with each other via non-fluorescent glycerin. The laser beam is led into the substrate 1 without reflecting on an interface of the prism 5 and the substrate 1. The mirror unit includes an automatic state, the angle and the position of which can be automatically adjusted, and a reflection mirror. The mirror unit is controlled by a mirror unit controller 6.

After the laser beam made incident on the substrate is shone on a sample on the substrate surface, a traveling direction of the laser beam is changed according to an angle of incidence of the laser beam. When the angle of incidence is smaller than a critical angle, the laser beam is not totally reflected on the substrate surface and is transmitted in the direction of the substrate surface (transmitted light). When the angle of incidence and the critical angle are equal, the laser beam diffuses on the substrate surface (surface diffusing light). When the angle of incidence is larger than the critical angle, the laser beam is totally reflected on the substrate surface (reflected light). At this point, evanescent light is generated very near the substrate surface. The critical angle is calculated by the following equation from a refractive index of the substrate and a refractive index of a medium present on the substrate surface.

$$\theta = \arcsin(n2/n1) \quad \text{(Equation)}$$

n1: refractive index of the substrate
n2: refractive index of the medium
n1>n2

Figure 2:
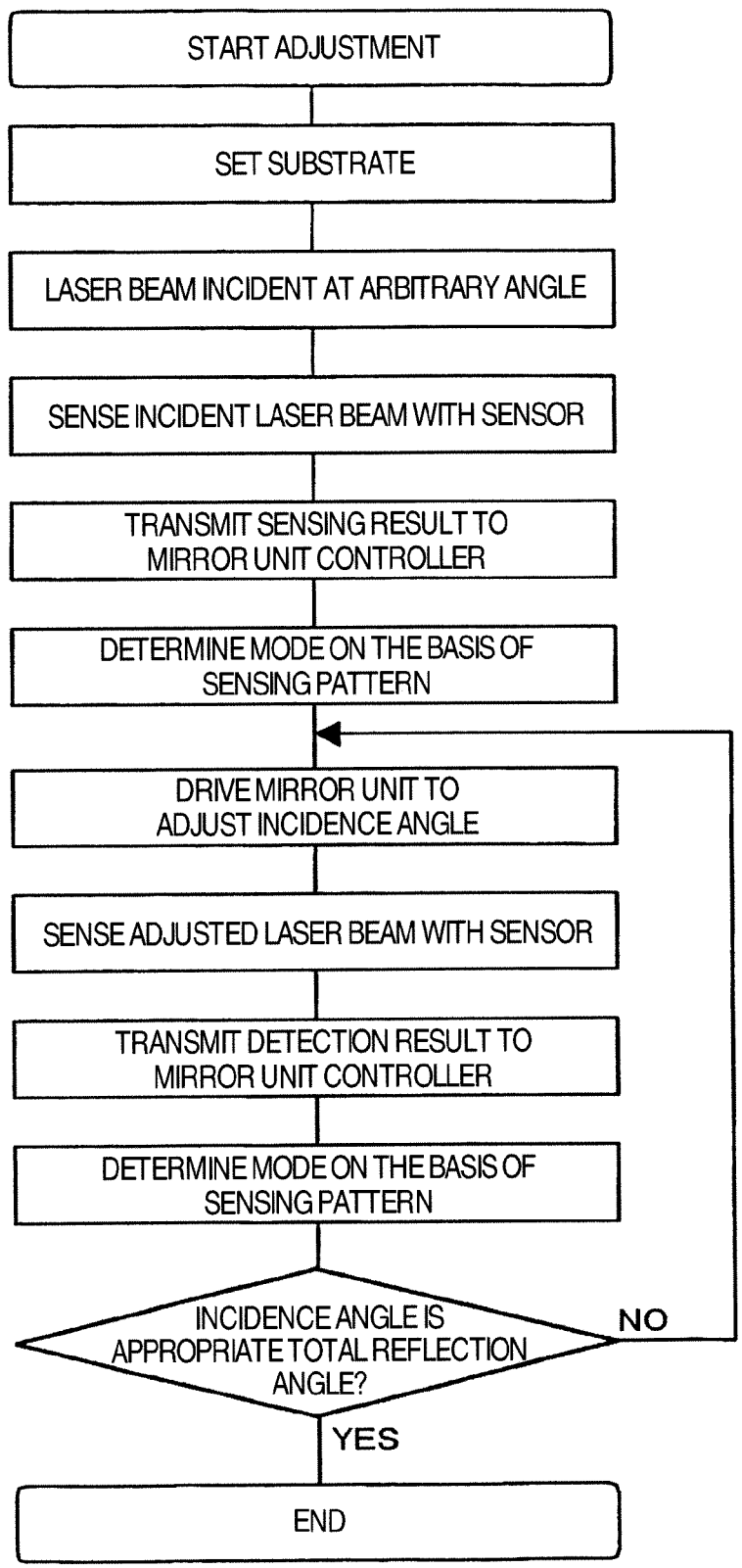
FIG. 2 is a flowchart of angle adjustment in the first embodiment.
Figure 3:
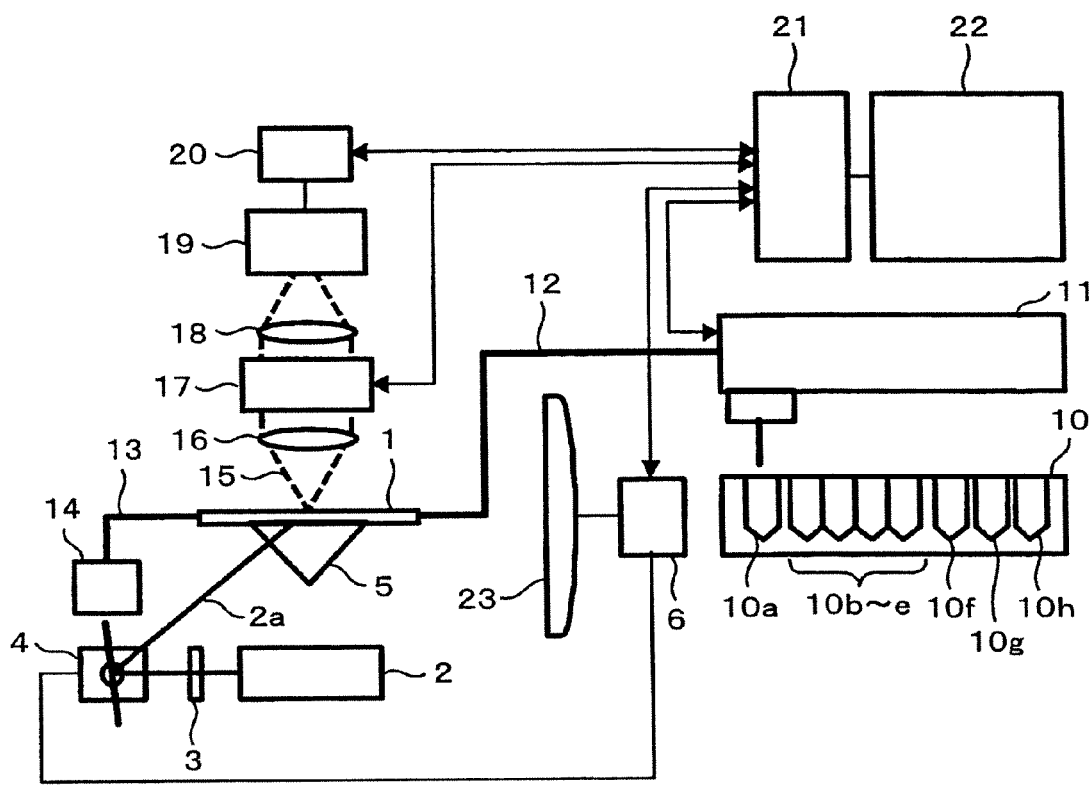
FIG. 3 is an explanatory diagram of a device in a second embodiment.
Figure 4:
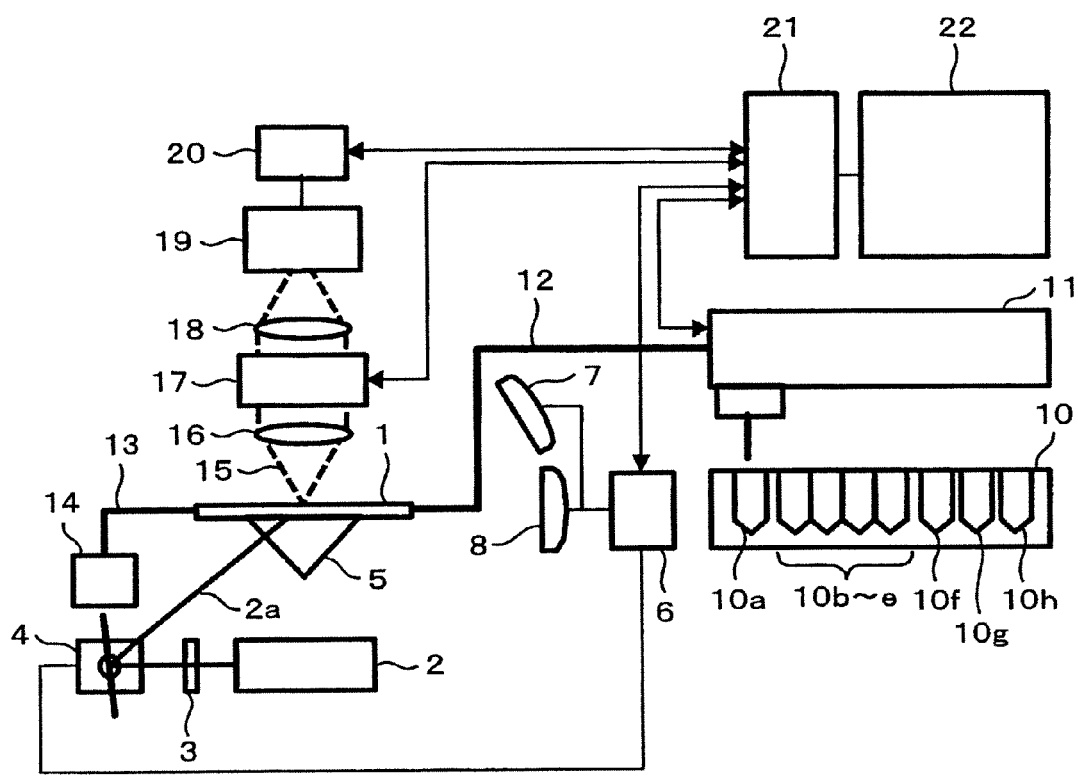
FIG. 4 is an explanatory diagram of a device in a third embodiment.
Figure 5:
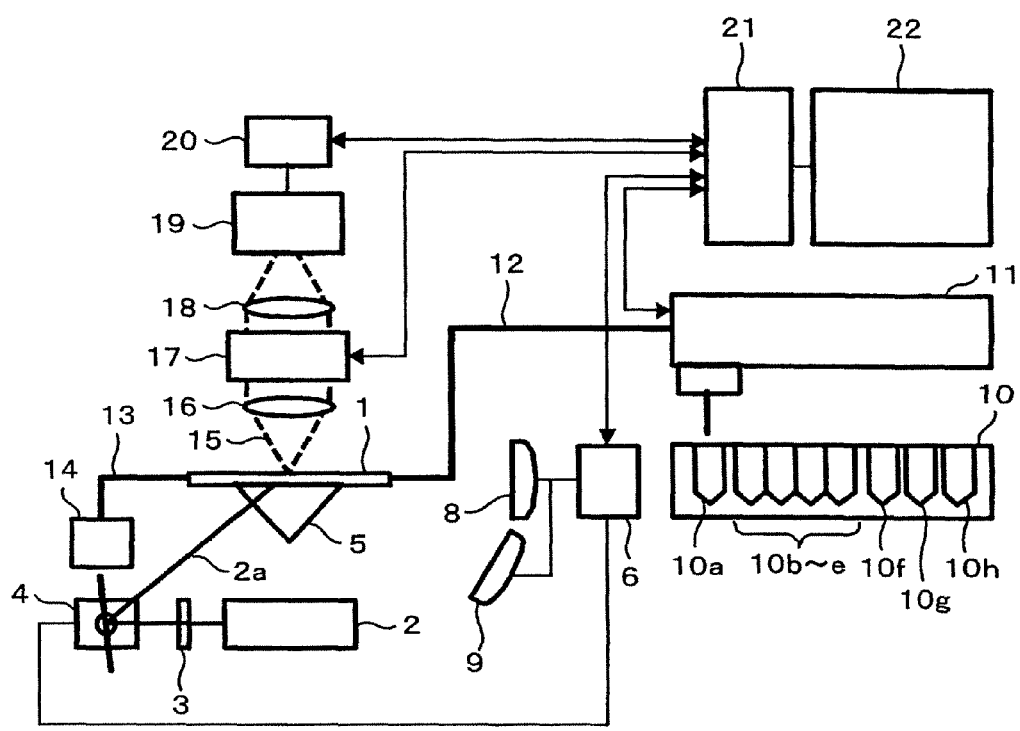
FIG. 5 is an explanatory diagram of a device in a fourth embodiment.
Figure 6:
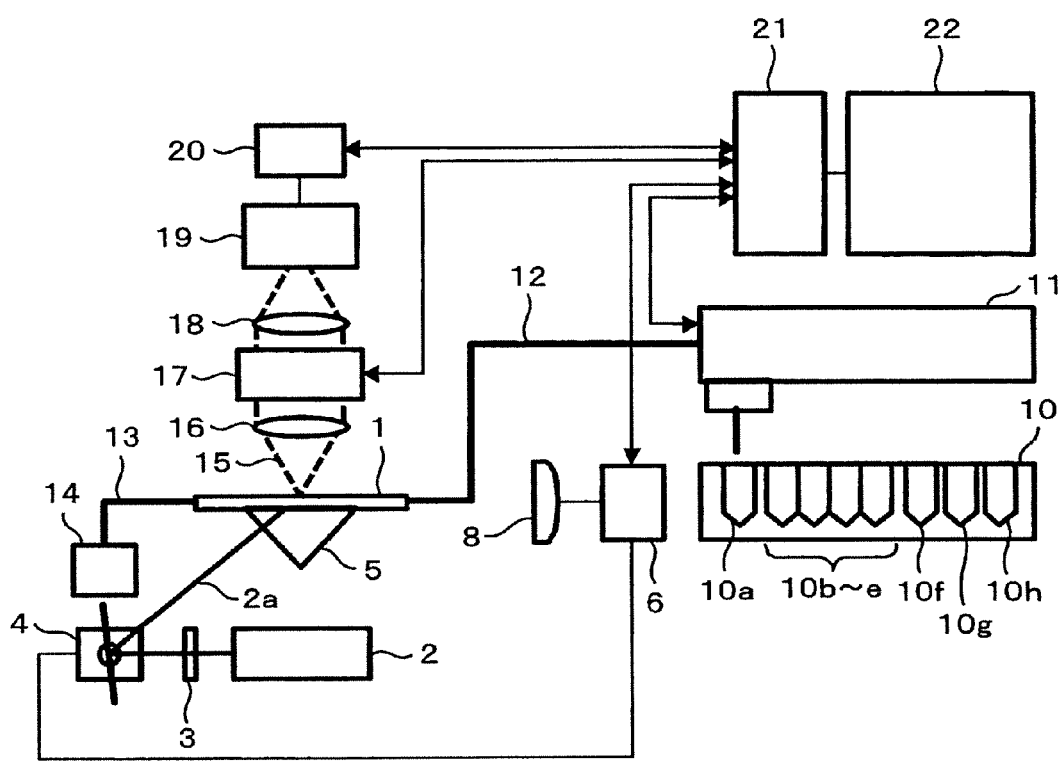
FIG. 6 is an explanatory diagram of a device in a fifth embodiment.

FIG. 2 is a flowchart during angle of incidence adjustment in this embodiment. A specific angle adjusting method is performed according to a procedure explained below. A laser beam is shone on a measurement area of the substrate surface at an arbitrary angle of incidence. The angle is, for example, 45 degrees. The laser beam after incidence is transmitted light, surface diffusing light, or totally reflected light according to a relation with the critical angle. Optical sensors 7, 8, and 9 for sensing transmitted light, surface diffusing light, and reflected light are set in the device. Sensing results of these sensors are sent to the mirror unit controller 6.

The mirror unit controller 6 drives the mirror unit 4 on the basis of information concerning the sensing results. Means for the driving is realized by an electric micrometer. Besides, a gonio stage, a galvanometer mirror, a polygon mirror, an acoustic optical element (AOM), and the like can be used. The mirror unit controller 6 includes five modes shown in a table below. The mirror unit controller 6 determines a mode according to a sensing pattern of the optical sensors 7, 8, and 9. The mirror unit 4 automatically performs adjustment according to a rule determined for each of the modes so that an angle of incidence is a total reflection angle. Alternatively, the mirror unit controller 6 issues an instruction for operation determined for each of the modes to the mirror unit 4. The mirror unit 4 operates according to this instruction and adjusts the angle of incidence so that the laser beam is totally reflected on the substrate surface.

"Signal is present" and "signal is absent" in the table do not indicate measurement values themselves but are signs indicating concepts of levels.

For example, when the substrate 1 is synthetic quartz and a medium is water, the critical angle is about 66 degrees. When a laser beam 2a is shone at an angle of incidence of 45 degrees, the laser beam 2a is transmitted through the substrate 1. At this point, a signal pattern of the optical sensors 7, 8, and 9 is (transmitted light, surface diffusing light, reflected light)=(1, 0, 0). Receiving this signal pattern, the mirror unit controller 6 determines a mode A and performs optical axis adjustment to increase the angle of incidence according to rules shown in the table below. Alternatively, receiving this signal pattern, the mirror unit controller 6 determines the mode A and issues an instruction to the mirror unit 4 to increase the angle of incidence.

When the angle of incidence reaches about 66 degrees, surface diffusing light is generated and the signal pattern of the optical sensors 7, 8, and 9 changes to (transmitted light, surface diffusing light, reflected light)=(0, 1, 0). Receiving this signal pattern, the mirror unit controller 6 determines a mode B and performs optical axis adjustment to further increase the angle of incidence according to the rules shown in the table below. Alternatively, receiving this signal pattern, the mirror unit controller 6 determines the mode B and issues an instruction to the mirror unit 4 to further increase the angle of incidence.

At an instance when the angle of incidence exceeds the critical angle, the surface diffusing light disappears and totally reflected light is generated instead. A signal pattern at this point is (transmitted light, surface diffusing light, reflected light)=(0, 0, 1). Receiving this signal pattern, the mirror unit controller 6 determines a mode C and stops the angle adjustment. Alternatively, receiving this signal pattern, the mirror unit controller 6 determines the mode C and issues an instruction for angle adjustment stop to the mirror unit 4.

For example, a critical angle in the case in which the substrate 1 is sapphire and a medium is the air is about 34 degrees. When the laser beam 2a is shone at an angle of incidence of 45 degrees, the laser beam 2a is totally reflected on the surface of the substrate 1. At this point, a signal pattern of the optical sensors 7, 8, and 9 is (transmitted light, surface diffusing light, reflected light)=(0, 0, 1). Receiving this signal pattern, the mirror unit controller 6 determines a mode D and performs optical axis adjustment to reduce the angle of incidence according to the rules shown in the table below. When the angle of incidence reaches 34 degrees, surface diffusing light is generated and the signal pattern of the optical sensors 7, 8, and 9 changes to (transmitted light, surface diffusing light, reflected light)=(0, 1, 0). Receiving this signal pattern, the mirror unit controller 6 determines the mode B and performs optical axis adjustment to increase the angle of incidence according to the rules shown in the table below. At an instance when the angle of incidence exceeds the critical angle, the surface diffusing light disappears and totally reflected light is generated instead. A signal pattern at this point is (transmitted light, surface diffusing light, reflected light)=(0, 0, 1). Receiving this signal pattern, the mirror unit controller 6 determines the mode C and stops the angle adjustment.

When a difference between a refractive index of the substrate 1 and a refractive index of a medium is larger or depending on a surface state of the substrate 1, for example, even in a transmission state, reflection partially occurs on the surface of the substrate 1. Therefore, in some case, the reflected light sensor 9 reacts in the modes A and B.

TABLE 1

Modes of Mirror Unit controller (First Embodiment)

| | Mode A | Mode B | Mode C | Mode D | Mode E (Initial state) |
|---|---|---|---|---|---|
| Magnitude relation between angle of incidence and critical angle | Angle of incidence < Critical angle (transmitted) | Angle of incidence = Critical angle (surface propagating) | Angle of incidence > Critical angle (totally reflected 1) | Angle of incidence > Critical angle (totally reflected 2) | Angle of incidence = 45 degrees |
| Excitation light sensor | 1 | 0 | 0 | 0 | — |
| Surface propagating light sensor | 0 | 1 | 0 | 0 | — |
| Reflected light sensor | 0 (or 1) | 0 (or 1) | 1 | 1 | — |
| Angle of incidence control | Increase angle of incidence to mode B | Increase angle of incidence to mode C | Stop angle of incidence driving | Reduce angle of incidence to mode B | 45 degrees with respect to substrate stage |
| Remarks | | | Shift only from mode B | | Selected only at start of adjustment |

*Signal is present: 1 Signal is absent: 0

With this adjusting mechanism, an angle of incidence of the laser beam 2a in the substrate 1 is always about 66 degrees (the angle varies according to a refractive index of the substrate 1 and a refractive index of a sample solution). The laser beam 2a is totally reflected on the surface of the substrate 1 to change to evanescent illumination. This makes it possible to perform fluorescence measurement at high S/N. A shining area of a laser is set to about 2 mm diameter.

A specific sequence analyzing method is performed according to a procedure explained below. A single-stranded nucleic acid is hybridized to the primers fixed on the substrate 1. A reaction is performed, for example, at 60° C. for ten minutes. A sequence of the primers only has to be partially complementary with the single-stranded nucleic acid. Base length of the primers is desirably equal to or larger than 10 in view of hybridization efficiency.

Subsequently, while labeled dATP, dTTP, dCTP, and dGTP are sequentially added, a base extension reaction is performed to decode a base sequence downstream of the primers. For example, first, a reaction solution containing Cy3-dATP and DNA polymerase (20 nM of Cy3-dATP, 0.1 U/μL of TaqDNA polymerase, 10 mM of Tris-HCl pH 7.8, and 2 mM of MgCl2) is caused to react with fragments on the substrate 1 for five minutes. Subsequently, unreacted Cy3-dATP is removed by a cleaning buffer (10 mM of Tris-HCl pH 7.8 and 2 mM of MgCl2).

Various reagents and buffers are stored in a reagent storage unit 10 and sent to the substrate via a dispensing unit 11 and through a liquid feeding tube 12. In the reagent storage unit 10, a reagent liquid container 10a, four kinds of labeling dNTP solution container 10b, 10c, 10d, and 10e, a dNTP mixture solution container 10f, a polymerase solution container 10g, a cleaning buffer container 10h, and the like are prepared. The reagent after reaction accumulates in a waste liquid container 14 through a waste liquid tube 13.

A YAG laser having wavelength of 532 nm is shone as excitation light to generate fluorescence 15 from the fragment in which the Cy3-dATP is captured. Since fluorescence generated from Cy3 molecules is quenched by irradiation of intense excitation light, it is desirable to perform observation at lower excitation light intensity during observation. Excitation light intensity is, for example, 1000 mW/mm$^2$. As means for suppressing quenching, addition of a deoxidation agent is also effective. This is because the quenching of the Cy3 molecules is caused by a reaction with dissolved oxygen in a solution. As the deoxidation agent, for example, peroxidase and superoxide dismutase can be used.

The fluorescence 15 is collected by a condenser lens (an objective lens) 16. Fluorescence having necessary wavelength is extracted by a filter unit 17. A fluorescent image is detected by an imaging lens 18 and a two-dimensional sensor camera 19. Plural filters corresponding to fluorescence to be detected are held in the filter unit 17. Control of the filter unit 17 is controlled by a control PC 21. For example, when dNTP added with four kinds of fluorescent dyes, it is possible to cope with the dNTP by, for example, switching filters for corresponding four kinds of phosphors with the filter unit 17 to detect fluorescent images. Setting of an exposure time of the two-dimensional sensor camera 19 and control of, for example, timing for capturing fluorescent images are performed by the control PC 21 via a two-dimensional sensor camera controller 20. The two-dimensional sensor camera 19 is, for example, an EM-CCD camera having pixel size of 16×16 μm and 512×512 pixels. An exposure time during fluorescence observation is 100 msec. Besides other general cooling CCD cameras, an imaging camera and the like such as a C-MOS area sensor can be used. The sensor is desirably a cooling type. By setting temperature to about −20° C. or lower, it is possible to reduce dark noise of the sensor and improve accuracy of measurement. Captured fluorescence observation data can be observed by a monitor 22.

The position of the fragment in which the Cy3-dATP is captured is specified on the basis of the fluorescence observation data to determine a sequence. After Cy3 fluorescence is observed, for example, intense excitation light is shone to prevent fluorescence deriving from the already-captured Cy3-dATP from occurring in the next step. The series of reaction steps explained above are performed in order of aATP, aTTP, dCTP, and dGTP. By performing this operation by 80 cycles, it is possible to decode about twenty to thirty based on a solid phase side of the fragments. In this embodiment, the Cy3 is used as a fluorescent dye and the YAG laser having wavelength of 532 nm is used as an excitation light source. However, a combination of a marking molecule and a light source is not limited to this.

In this embodiment, base sequence decoding by sequential reactions is performed by using one kind of a fluorescent dye. However, another method may be used. For example, when labeling dNTP obtained by combining different four kinds of fluorescent dyes via nitrobenzyl is used for 3'-OH acid of four kinds of dNTP, the kinds of dNTP do not have to be caused to react one by one as in this embodiment. In other words, at a stage when a fluorescent dye of the 3'-OH acid changes to a protecting group and capturing is performed, an extension reaction after that does not proceed. Decoding of a base sequence is performed by making use of this fact. For example, a reaction solution containing four kinds of fluorescence labeling dNTP and DNA polymerase (20 nM of fluorescent labeling dNTP mixture, 0.1 U/μL of TaqDNA polymerase, 10 mM of Tris-HCl pH 7.8, and 2 mM of MgCl2) is caused to react with the fragments on the substrate 1 for five minutes. Subsequently, non-reacting fluorescent labeling dNTP is removed by a cleaning buffer (10 mM of Tris-HCl pH 7.8 and 2 mM of MgCl2). Excitation light is shone, the four kinds of fluorescence are observed by a two-dimensional sensor camera, fragments in which the respective kinds of fluorescent labeling dNTP are captured are specified, and a sequence is determined. As the four kinds of fluorescent dyes, for example, Cy3, Cy5, Cy5.5, and Alexa fluor (registered trademark) 488 can be used. To prevent cross-contamination of fluorescence, it is desirable to select fluorescent dyes in fluorescent wavelength bands apart from one another as much as possible. As the excitation light, excitation light sources suitable for wavelength characteristics of the respective fluorescent dyes are used or target wavelength components are separated from multi-wavelength light and used by using a band-pass filter or the like. Similarly, fluorescence is observed by separating target wavelength components using a band-pass filter or the like suitable for the wavelength characteristics of the respective fluorescent dyes. After the observation, the fluorescent dyes are separated by chemical or physical means and the 3'-OH acid of the fluorescent labeling dNTP captured immediately before the observation is released. The separating means is, for example, UV irradiation having wavelength of 360 nm or less. The separated fluorescent dyes are removed by the cleaning buffer. It is possible to decode a base sequence by performing the series of operation plural times.

In this embodiment, the four kinds of fillers in the filler unit 17 are switched to measure fluorescence wavelength in order. However, it is also possible to simultaneously measure four kinds of fluorescence wavelength. For example, if a two-dimensional spectral unit is used instead of the filter unit, it is possible to perform multi-color measurement in a two-dimensional image. In this case, it is desirable that primers are regularly arranged on a substrate. For example, if prisms or the like are arranged in an optical system as the two-dimensional spectral unit and color is dispersed in one direction of an image, it is possible to simultaneously detect fluorescence from respective primer positions and simultaneously detect four or more wavelength bands. Dispersion width is set smaller than an arraying pitch of the primers. In this method, it is also possible to cause the reaction solution to continuously react and continuously measure fluorescent wavelength.

According to the operation explained above, concerning the device that performs fluorescence observation using total reflection illumination, an angle of incidence of excitation light is adjusted so that the excitation light is always totally reflected on a substrate surface irrespective of an angle of the substrate surface. In this embodiment, the adjustment of the angle of incidence is performed in an observation area. However, the adjustment may be performed in another area. For example, when a substrate on which a fluorescent sample is already fixed is observed, by performing the angle of incidence adjustment near a sample fixed area, it is possible to prevent fluorescence of a measurement sample from being quenched by irradiation of a laser beam involved in the adjustment.

It is also possible to measure and store in advance adjustment parameters of the entire substrate, i.e., for each of positions of the substrate and, when measurement positions of the substrate are changed, continuously perform the angle of incidence adjustment on the basis of the stored data.

According to this embodiment, manual adjustment operation for a total reflection angle is unnecessary and operability is improved compared with the conventional method. Since it is possible to always keep the total reflection angle constant without being affected by waviness or the like of the substrate surface, stability and reliability are improved compared with the conventional method.

[Second Embodiment]

In the first embodiment, transmitted light, surface diffusing light, a reflected light are sensed by the three optical sensors. However, it is also possible to sense the three lights with one optical sensor 23. Specifically, the three kinds of light are respectively led to sectioned three areas of the optical sensor 23 directly or by an optical element such as a mirror. A sensing result of the optical sensor 23 is sent to the mirror unit controller 6. The mirror unit controller 6 drives the mirror unit 4 on the basis of the information. As in the first embodiment, the mirror unit controller 6 includes five modes. The mirror unit 4 automatically performs adjustment according to rules determined for each of the modes so that an angle of incidence is a total reflection angle. Alternatively, as in the first embodiment, the mirror unit controller 6 includes five modes and determines a mode according to a sensing pattern of the optical sensor 23. The mirror unit controller 6 issues an instruction for operation determined for each of the modes to the mirror unit 4. The mirror unit 4 operates according to this instruction and adjusts an angle of incidence so that a laser beam is totally reflected on a substrate surface.

[Third Embodiment]

In the first embodiment, the three lights of transmitted light, surface diffusing light, and reflected light are sensed. However, lights to be sensed can also be two lights of transmitted light and surface diffusing light. As in the first embodiment, the laser beam 2a is shone at an arbitrary angle of incidence on a measurement area on the surface of the substrate 1. The angle is, for example, 45 degrees. The optical sensors 7 and 8 for sensing transmitted light and surface diffusing light are set in the device. Sensing results of these sensors are sent to the mirror unit controller 6. The mirror unit controller 6 drives the mirror unit 4 on the basis of the information. The driving is performed by means same as that in the first embodiment. The mirror unit controller 6 includes five modes shown in a table below and determines a mode according to a sensing pattern of the optical sensors 7 and 8. The mirror unit 4 automatically performs adjustment according to rules determined for each of the modes so that an angle of incidence is a total reflection angle. Alternatively, as in the first embodiment, the mirror unit controller 6 includes five modes and determines a mode according to a sensing pattern of the optical sensors 7 and 8. The mirror unit controller 6 issues an instruction for operation determined for each of the modes to the mirror unit 4. The mirror unit 4 operates according to this instruction and adjusts an angle of incidence so that a laser beam is totally reflected on a substrate surface.

For example, when the substrate 1 is synthetic quartz and a medium is water, a critical angle is about 66 degrees. When the laser beam 2a is shone at an angle of incidence of 45 degrees, the laser beam 2a is transmitted through the substrate 1. At this point, a signal pattern of the optical sensors 7 and 8 is (transmitted light, surface diffusing light)=(1, 0). Receiving this signal pattern, the mirror unit controller 6 determines a mode A and performs optical axis adjustment to increase the angle of incidence according to rules shown in the table below. Alternatively, receiving this signal pattern, the mirror unit controller 6 determines the mode A and issues an instruction to the mirror unit 4 to increase the angle of incidence.

When the angle of incidence reaches about 66 degrees, surface diffusing light is generated and the signal pattern of the optical sensors 7 and 8 changes to (transmitted light, surface diffusing light)=(0, 1). Receiving this signal pattern, the mirror unit controller 6 determines a mode B and performs optical axis adjustment to further increase the angle of incidence according to the rules shown in the table below. Alternatively, receiving this signal pattern, the mirror unit controller 6 determines the mode B and issues an instruction to the mirror unit 4 to further increase the angle of incidence.

At an instance when the angle of incidence exceeds the critical angle, the surface diffusing light disappears and totally reflected light is generated instead. A signal pattern at this point is (transmitted light, surface diffusing light)=(0, 0). Receiving this signal pattern, the mirror unit controller 6 determines a mode C and stops the angle adjustment. Alternatively, receiving this signal pattern, the mirror unit controller 6 determines the mode C and issues an instruction for angle adjustment stop to the mirror unit 4.

In this embodiment, the optical sensors for transmitted light and surface diffusing light are separately prepared. However, as in the second embodiment, a method of leading light to sectioned two areas of one optical sensor may be adopted.

TABLE 2

Modes of Mirror Unit controller (Third Embodiment)

|  | Mode A | Mode B | Mode C | Mode D | Mode E (Initial state) |
|---|---|---|---|---|---|
| Magnitude relation between angle of incidence and critical angle | Angle of incidence < Critical angle (transmitted) | Angle of incidence = Critical angle (surface propagating) | Angle of incidence > Critical angle (totally reflected 1) | Angle of incidence > Critical angle (totally reflected 2) | Angle of incidence = 45 degrees |
| Excitation light sensor | 1 | 0 | 0 | 0 | — |
| Surface propagating light sensor | 0 | 1 | 0 | 0 | — |
| Angle of incidence control | Increase angle of incidence to mode B | Increase angle of incidence to mode C | Stop angle of incidence driving | Reduce angle of incidence to mode B | 45 degrees with respect to substrate stage |
| Remarks |  |  | Shift only from mode B |  | Selected only at start of adjustment |

*Signal is present: 1 Signal is absent: 0

[Fourth Embodiment]

In the first embodiment, the three lights of transmitted light, surface diffusing light, and reflected light are sensed. However, light to be sensed can also be realized by two lights of surface transmitted light and reflected light. As in the first embodiment, the laser beam 2a is shone at an arbitrary angle of incidence on a measurement area on the surface of the substrate 1. The angle is, for example, 45 degrees. The optical sensors 8 and 9 for sensing surface diffusing light and reflected light are set in the device. Sensing results of these sensors are sent to the mirror unit controller 6. The mirror unit controller 6 drives the mirror unit 4 on the basis of the information. The driving is performed by means same as that in the first embodiment. The mirror unit controller 6 includes five modes shown in a table below and determines a mode according to a sensing pattern of the optical sensors 8 and 9. The mirror unit 4 automatically performs adjustment according to rules determined for each of the modes so that an angle of incidence is a total reflection angle. Alternatively, as in the first embodiment, the mirror unit controller 6 includes five modes and determines a mode according to a sensing pattern of the optical sensors 8 and 9. The mirror unit controller 6 issues an instruction for operation determined for each of the modes to the mirror unit 4. The mirror unit 4 operates according to this instruction and adjusts an angle of incidence so that a laser beam is totally reflected on a substrate surface.

For example, when the substrate 1 is synthetic quartz and a medium is water, a critical angle is about 66 degrees. When the laser beam 2a is shone at an angle of incidence of 45 degrees, the laser beam 2a is transmitted through the substrate 1. At this point, a signal pattern of the optical sensors 8 and 9 is (surface diffusing light, reflected light)=(0, 0). Receiving this signal pattern, the mirror unit controller 6 determines a mode A and performs optical axis adjustment to increase the angle of incidence according to rules shown in the table below. Alternatively, receiving this signal pattern, the mirror unit controller 6 determines the mode A and issues an instruction to the mirror unit 4 to increase the angle of incidence.

When the angle of incidence reaches about 66 degrees, surface diffusing light is generated and the signal pattern of the optical sensors 8 and 9 changes to (surface diffusing light, reflected light)=(1, 0). Receiving this signal pattern, the mirror unit controller 6 determines a mode B and performs optical axis adjustment to further increase the angle of incidence according to the rules shown in the table below. Alternatively, receiving this signal pattern, the mirror unit controller 6 determines the mode B and issues an instruction to the mirror unit 4 to increase the angle of incidence.

At an instance when the angle of incidence exceeds the critical angle, the surface diffusing light disappears and totally reflected light is generated instead. A signal pattern at this point is (surface diffusing light, reflected light)=(0, 1). Receiving this signal pattern, the mirror unit controller 6 determines a mode C and stops the angle adjustment. Alternatively, receiving this signal pattern, the mirror unit controller 6 determines the mode C and issues an instruction for angle adjustment stop to the mirror unit 4. In this embodiment, the optical sensors for surface diffusing light and reflected light are separately prepared. However, as in the second embodiment, a method of leading light to sectioned two areas of one optical sensor may be adopted.

optical sensor 8. The mirror unit 4 automatically performs adjustment according to rules determined for each of the modes so that an angle of incidence is a total reflection angle. Alternatively, the mirror unit controller 6 includes the four modes shown in the table below and determines a mode according to a sensing pattern of the optical sensor 8. The mirror unit controller 6 issues an instruction for operation determined for each of the modes to the mirror unit 4. The mirror unit 4 operates according to this instruction and adjusts an angle of incidence so that a laser beam is totally reflected on a substrate surface.

For example, when the substrate 1 is synthetic quartz and a medium is water, a critical angle is about 66 degrees. When the laser beam 2a is shone at an angle of incidence of 90 degrees, the laser beam 2a is transmitted through the substrate 1. At this point, a signal pattern of the optical sensor 8 is (surface diffusing light)=(0). Receiving this signal pattern, the mirror unit controller 6 determines a mode A and performs optical axis adjustment to increase the angle of incidence according to rules shown in the table below. Alternatively, receiving this signal pattern, the mirror unit controller 6 determines the mode A and issues an instruction to the mirror unit 4 to increase the angle of incidence.

When the angle of incidence reaches 66 degrees, surface diffusing light is generated and the signal pattern of the optical sensor 8 changes to (surface diffusing light)=(1). Receiving this signal pattern, the mirror unit controller 6 determines a mode B and performs optical axis adjustment to further increase the angle of incidence according to the rules shown

TABLE 3

Modes of Mirror Unit controller (Fourth Embodiment)

|  | Mode A | Mode B | Mode C | Mode D | Mode E (Initial state) |
|---|---|---|---|---|---|
| Magnitude relation between angle of incidence and critical angle | Angle of incidence < Critical angle (transmitted) | Angle of incidence = Critical angle (surface propagating) | Angle of incidence > Critical angle (totally reflected 1) | Angle of incidence > Critical angle (totally reflected 2) | Angle of incidence = 45 degrees |
| Surface propagating light sensor | 0 | 1 | 0 | 0 | — |
| Reflected light sensor | 0 (or 1) | 0 (or 1) | 1 | 1 | — |
| Angle of incidence control | Increase angle of incidence to mode B | Increase angle of incidence to mode C | Stop angle of incidence driving | Reduce angle of incidence to mode B | 45 degrees With respect to substrate stage |
| Remarks |  |  | Shift only from mode B |  | Selected only at start of adjustment |

*Signal is present: 1 Signal is absent: 0

[Fifth Embodiment]

In the first embodiment, the three lights of transmitted light, surface diffusing light, and reflected light are sensed. However, light to be sensed can also be realized by only surface diffusing light. As in the first embodiment, the laser beam 2a is shone at an angle of incidence of 90 degrees on a measurement area on the surface of the substrate 1. The optical sensor 8 for sensing surface diffusing light is set in the device. A sensing result of this sensor is sent to the mirror unit controller 6. The mirror unit controller 6 drives the mirror unit 4 on the basis of the information. The driving is performed by means same as that in the first embodiment. The mirror unit controller 6 includes four modes shown in a table below and determines a mode according to a sensing pattern of the in the table below. Alternatively, receiving this signal pattern, the mirror unit controller 6 determines the mode B and issues an instruction to the mirror unit 4 to increase the angle of incidence.

At an instance when the angle of incidence exceeds the critical angle, the surface diffusing light disappears and totally reflected light is generated instead. A signal pattern at this point is (surface diffusing light)=(0). Receiving this signal pattern, the mirror unit controller 6 determines a mode C and stops the angle adjustment. Alternatively, receiving this signal pattern, the mirror unit controller 6 determines the mode C and issues an instruction for angle adjustment stop to the mirror unit 4.

TABLE 4

Modes of Mirror Unit controller (Fifth Embodiment)

| | Mode A | Mode B | Mode C | Mode E (Initial state) |
|---|---|---|---|---|
| Magnitude relation between angle of incidence and critical angle | Angle of incidence < Critical angle (transmitted) | Angle of incidence = Critical angle (surface propagating) | Angle of incidence > Critical angle (totally reflected 1) | Angle of incidence = 90 degrees |
| Surface propagating light sensor | 0 | 1 | 0 | — |
| Angle of incidence control | Increase angle of incidence to mode B | Increase angle of incidence to mode C | Stop angle of incidence driving | 90 degrees with respect to substrate stage |
| Remarks | | | Shift only from mode B | Selected only at start of adjustment |

*Signal is present: 1 Signal is absent: 0

INDUSTRIAL APPLICABILITY

The present invention is useful for monomolecular fluorescence observation. Therefore, the present invention can be widely used in the life science field including biology, chemical, and medical fields.

REFERENCE SIGNS LIST

| | |
|---|---|
| 1 | substrate |
| 2 | laser device |
| 2a | laser beam |
| 3 | quarter-wave plate |
| 4 | mirror unit |
| 5 | prism |
| 6 | mirror unit controller |
| 7 | optical sensor for transmitted light |
| 8 | optical sensor for surface diffusing light |
| 9 | optical sensor for reflected light |
| 10 | reagent storage unit |
| 10a | sample liquid container |
| 10b, 10c, 10d, 10e | labeling dNTP solution containers |
| 10f | dNTP mixture solution container |
| 10h | cleaning buffer container |
| 10g | polymerase solution container |
| 11 | dispensing unit |
| 12 | liquid feeding tube |
| 13 | waste liquid tube |
| 14 | waste liquid container |
| 15 | fluorescence |
| 16 | objective lens |
| 17 | filter unit |
| 18 | imaging lens |
| 19 | two-dimensional sensor camera |
| 20 | two-dimensional sensor camera controller |
| 21 | control PC |
| 22 | monitor |
| 23 | optical sensor |

The invention claimed is:

1. A total internal reflection fluorescence (TIRF) observation device comprising,
a substrate, on a surface of which a sample is mounted to be measured,
an optical source for irradiating the substrate with an excitation light,
a detector for detecting a light emitted from the substrate,
an optical sensor for detecting a transmitted light, a surface diffusing light, and a reflected light generated from the excitation light after the substrate is irradiated with the excitation light,
a controller for measuring a condition of an incidence angle of the excitation light from a combination of detected results of the transmitted light, the surface diffusing light, and the reflected light obtained by the optical sensor, and
an adjustor for adjusting the incidence angle of the excitation light in accordance with a measured result of the controller.

2. The total internal reflection fluorescence (TIRF) observation device according to claim 1, wherein the substrate is made of an optically transparent material.

3. A total internal reflection fluorescence (TIRF) observation device comprising,
a substrate on a surface of which a specimen is mounted to be measured,
an optical source for irradiating the substrate with an excitation light,
a detector for detecting a light emitted from the substrate,
an optical sensor for detecting the excitation light after the substrate is irradiated with the excitation light,
an adjustor for adjusting an incidence angle of the excitation light in accordance with a detection result of the optical sensor, and
a controller including an algorithm for ordering a next action of the adjustor on the basis of a present condition of the angle of incidence.

4. The total internal reflection fluorescence observation device according to claim 3, wherein the substrate is made of an optically transparent material.

5. A method for adjusting automatically an angle of incidence of an excitation light in a device for observing a fluorescence a using total reflection illumination, comprising the steps of:
changing continuously the angle of incidence of the excitation light with respect to a substrate on a surface of which substrate a sample is mounted to be measured,
detecting with at least one optical sensor, a transmitted light, a surface diffusing light and a reflected light generated by irradiating the substrate with the excitation light,
measuring with a controller, a condition of the incidence angle of the excitation light from a combination of detected results of the transmitted light, the surface diffusing light, and the reflected light obtained by the optical sensor, and
adjusting with an angle of incidence controlling mechanism on the basis of a measured result of the controller, the angle of incidence to be made equivalent to a total reflection angle.

6. A method for adjusting automatically an angle of incidence of an excitation light in a device for observing a fluorescence using a total reflection illumination, comprising the steps of:
changing continuously the angle of incidence of the excitation light with respect to a substrate on a surface of which substrate a sample is mounted to be measured,
detecting with at least one optical sensor, a transmitted light and a surface diffusing light generated by irradiating the substrate with the excitation light,
measuring with a controller, a condition of the incidence angle of the excitation light from a combination of detected results of the transmitted light and the surface diffusing light obtained by the optical sensor, and adjusting with an angle of incidence controlling mechanism on the basis of a measured result of the controller, the angle of incidence to be made equivalent to a total reflection angle.

7. A method for adjusting automatically an angle of incidence of an excitation light in a device for observing a fluorescence using a total reflection illumination, comprising the steps of:

changing continuously the angle of incidence of the excitation light with respect to a substrate on a surface of which substrate a sample is mounted to be measured, detecting with at least one optical sensor, a surface diffusing light and a reflected light generated by irradiating the substrate with the excitation light, measuring with a controller, a condition of the incidence angle of the excitation light from a combination of detected results of the surface diffusing light and the reflected light obtained by the optical sensor and adjusting with an angle of incidence controlling mechanism on the basis of a measured result of the controller, the angle of incidence to be made equivalent to a total reflection angle.

8. A method for adjusting automatically an angle of incidence of an excitation light in a device for observing a fluorescence using a total reflection illumination, comprising the steps of:

changing continuously the angle of incidence of the excitation light with respect to a substrate on a surface of which substrate a sample is mounted to be measured, detecting with at least one optical sensor, a surface diffusing light generated by irradiating the substrate with the excitation light, measuring with a controller, a condition of the incidence angle of the excitation light from a detected result of the surface diffusing light obtained by the optical sensor, and adjusting with an angle of incidence controlling mechanism on the basis of a measured result of the controller, the angle of incidence to be made equivalent to a total reflection angle.

9. A method for adjusting automatically an incidence angle of an excitation light in a device for observing fluorescence using a total reflection illumination comprising the steps of:

changing continuously the incidence angle of the excitation, light with respect to a substrate on a surface of which substrate a specimen is mounted to be measured, detecting with at least one optical sensor, a transmitted light, a surface diffusing light, and a reflected light generated by the substrate with the excitation light, and adjusting with an incidence angle controlling mechanism on the basis of detected results of the optical sensor, the incidence angle, wherein a controller orders along an algorithm included by the controller a next action of the incidence angle controlling mechanism on the basis of a present condition of the incidence angle, and the incidence angle controlling mechanism adjusts along the ordered next action the incidence angle to be made equivalent to a total reflection angle.

10. A method for adjusting automatically an incidence angle of an excitation light in a device for observing a fluorescence using a total reflection illumination, comprising the steps of :

changing continuously the incidence angle of the excitation light with respect to a substrate on a surface of which substrate a specimen is mounted to be measured detecting with at least one optical sensor, a transmitted light and a surface diffusing light generated by irradiating the substrate with the excitation light, and adjusting with an incidence angle controlling mechanism on the basis of detected results of the optical sensor the incidence angle, wherein a controller orders along an algorithm included by the controller a next action of the incidence angle controlling mechanism on the basis of a present condition of the incidence angle and the incidence angle controlling mechanism adjusts along the ordered next action the incidence angle to be made equivalent to a total reflection angle.

11. A method for adjusting automatically an incidence angle of an excitation light in a device for observing a fluorescence using a total reflection illumination, comprising the steps of:

changing continuously the incidence angle of the excitation light with respect to a substrate on a surface of which substrate a specimen is mounted to be measured, detecting with at least one optical sensor, a surface diffusing light, and a reflected light generated by irradiating the substrate with the excitation light, and adjusting with an incidence angle controlling mechanism on the basis of detected results of the optical sensor, the incidence angle, wherein a controller orders along an algorithm included by the controller a next action of the incidence angle controlling mechanism on the basis of a present condition of the incidence angle, and the incidence angle controlling mechanism adjusts along the ordered next action the incidence angle to be made equivalent to a total reflection angle.

12. A method for adjusting automatically an incidence angle of an excitation light in a device for observing a fluorescence using a total reflection illumination, comprising the steps of:

changing continuously the incidence angle of the excitation light with respect to a substrate on a surface of which substrate a specimen is mounted to be measured, detecting with at least one optical sensor, a surface diffusing light generated by irradiating the substrate with the excitation light, and adjusting with an incidence angle controlling mechanism on the basis of a detected result of the optical sensor, the incidence angle, wherein a controller orders along an algorithm included by the controller a next action of the incidence angle controlling mechanism on the basis of a present condition of the incidence angle, and the incidence angle controlling mechanism adjusts along the ordered next action the incidence angle to be made equivalent to a total reflection angle.

* * * * *